(12) United States Patent
Magill et al.

(10) Patent No.: US 8,177,789 B2
(45) Date of Patent: May 15, 2012

(54) DISTRACTION OSTEOGENESIS METHODS AND DEVICES

(75) Inventors: John C. Magill, Woburn, MA (US);
Joseph R. Morency, Salem, MA (US);
Leonard B. Kaban, Charlestown, MA (US); Maria Troulis, Charlestown, MA (US)

(73) Assignee: The General Hospital Corporation, Andover, MA (US)

( * ) Notice: Subject to any disclaimer, the term of this patent is extended or adjusted under 35 U.S.C. 154(b) by 830 days.

(21) Appl. No.: 12/242,056

(22) Filed: Sep. 30, 2008

(65) Prior Publication Data

US 2009/0088766 A1   Apr. 2, 2009

Related U.S. Application Data

(60) Provisional application No. 60/976,643, filed on Oct. 1, 2007.

(51) Int. Cl.
*A61B 17/60*   (2006.01)

(52) U.S. Cl. .................................................. 606/105

(58) Field of Classification Search .............. 606/54–55, 606/57–58, 60, 62–63, 71, 105; 433/7; 91/363 R, 91/361; *A61B 17/60*
See application file for complete search history.

(56) References Cited

U.S. PATENT DOCUMENTS

| | | | |
|---|---|---|---|
| 5,536,269 A * | 7/1996 | Spievack .......................... | 606/63 |
| 5,626,581 A | 5/1997 | Staehlin et al. | |
| 5,700,263 A * | 12/1997 | Schendel ......................... | 606/57 |
| 6,033,412 A | 3/2000 | Losken et al. | |
| 6,113,599 A * | 9/2000 | Landsberger .................... | 606/60 |
| 6,277,124 B1 | 8/2001 | Haag | |
| 6,423,069 B1 | 7/2002 | Sellers | |
| 6,565,576 B1 | 5/2003 | Stauch et al. | |
| 6,673,079 B1 | 1/2004 | Kane | |
| 6,918,910 B2 | 7/2005 | Smith et al. | |
| 2006/0037467 A1 * | 2/2006 | McCarroll et al. .............. | 91/361 |
| 2008/0161861 A1 * | 7/2008 | Huebner ........................ | 606/286 |

FOREIGN PATENT DOCUMENTS

DE       19645392       4/1998

OTHER PUBLICATIONS

International Search Report (PCT/US2008/078318) dated Jan. 29, 2009.
Currie et al., British Journal of Plastic Surgery, "Cranial distraction osteogenesis in sheep using a totally implantable hydraulic mechanism: early results," vol. 54(5):385-389 (2001).
Kessler et al., Journal of Cranio-Maxillofacial Surgery, "A new distraction device to compare continuous and discontinuous bone distraction in mini-pigs; a preliminary report," vol. 28:5-11 (2000).
Kessler et al., Dept. of Oral and Maxillofacial Surgery, Plastic and Reconstructive Surgery, "The effects of magnitude and frequency of distraction forces on tissue regeneration in distraction osteogenesis of the mandible," pp. 171-180 (2002).

* cited by examiner

*Primary Examiner* — Thomas C. Barrett
*Assistant Examiner* — Christian Sevilla
(74) *Attorney, Agent, or Firm* — Nutter McClennen & Fish LLP; Thomas J. Engellenner; Rory P. Pheiffer

(57) ABSTRACT

Methods and devices for distraction osteogenesis are disclosed employing an energy storage device and a controlled release of energy to provide a separating force. For example, bone expansion devices can include a first anchor element attachable to a first segment of bone, a second anchor element attachable to a second segment of bone, and an actuator for applying a separating force between the first and second anchor elements. The actuator can include a potential energy storage device and a controller for releasing energy from the energy storage device to provide the separating force.

20 Claims, 5 Drawing Sheets

DISTRACTION OSTEOGENESIS METHODS AND DEVICES

FEDERALLY SPONSORED RESEARCH

This invention was made with government support from the National Institutes of Health under Grant No. 1 R43DE014803-01A1. The government has certain rights in this invention.

TECHNICAL FIELD

The technical field of this invention is distraction osteogenesis and, in particular, methods and devices for expansion of bone and skeletal structures, such as the mandible.

BACKGROUND OF THE INVENTION

Skeletal expansion to treat deformities, such as maxillofacial deformities, is accomplished conventionally through multiple bone grafts. However, a new approach is distraction osteogenesis, a technique which employs the body's bone regeneration ability to fill a gap in the bone. The gap is gradually expanded with a mechanical distractor as new bone tissue is grown, thus reducing or eliminating the need for bone grafts.

However, existing distractors typically are manually operated devices that require daily adjustment by the patient or a healthcare professional. Such adjustments are typically done empirically or based on a predetermined schedule that may bear little relationship to a patient's actual tissue regenerating capabilities. Moreover, conventional distractors are linear devices that usually only permit bone expansion in a straight line while optimal bone reconstruction, especially facial bone reconstruction, may require non-linear, e.g., curved, expansion techniques.

Accordingly, there exists a need for better bone distraction methods and devices. Better control mechanisms, especially automated systems and devices that permit greater degrees of dimensional freedom would satisfy long-felt needs in the art.

SUMMARY OF THE INVENTION

Methods and devices are disclosed for distraction osteogenesis employing an energy storage device and a controlled release of energy to provide a separating force. Bone expansion devices according to the invention can include a first anchor element adapted to be attached to a first segment of bone, a second anchor element adapted to be attached to a second segment of bone, and an actuator for applying a separating force between the first and second anchor elements, the actuator further comprising a potential energy storage device and a controller for releasing energy from the energy storage device to provide the separating force.

In one embodiment the first anchor element can include a rail and the second anchor element can be mechanically linked to the rail of the first anchor element, e.g., such the second anchor element is slidably coupled to the rail of the first anchor element. In further embodiments, the rail can be either straight or curved, depending upon the application. Alternatively, the rail can be slidably coupled to the second anchor element such that the rail can slide between a contracted and an extended position. In further embodiments, the rail can be either straight or curved, depending upon the application.

The actuators of the invention can be hydraulic actuators, e.g., a chamber coupled to one of the anchor elements and a piston disposed within the chamber and mechanically linked to the other anchor element such that a fluid within the chamber can apply a separating force. In one embodiment, the actuator can further include an energy source for pressurizing the fluid within the chamber. For example, the energy source can include a reservoir of pressurized fluid and the reservoir can be pre-charged with the pressurized fluid. In another embodiment, the energy source can include a spring that applies pressure to the fluid.

The actuator can further include a valve for regulating fluid transfer (volume and/or pressure) from the reservoir to the chamber. Additionally, the invention can include one or more sensors for measuring separation of the first and second anchor elements and the controller can further include a microprocessor.

In another aspect of the invention, kits are disclosed for distraction osteogenesis that can include a plurality of base elements adapted to be attached to a first segment of bone, each of said base elements having a rail of a different shape, at least one rail receiving element adapted to be attached to a second segment of bone and further adapted to have a base element rail slidably coupled thereto, and a actuator for applying a separating force between a base element and a slider element, the actuator further comprising a potential energy storage device and a controller for incrementally releasing energy from the energy storage device to provide the separating force.

In a further aspect of the invention, methods for distraction osteogenesis are disclosed that can include the steps of providing a first anchor element, a second anchor element, and a actuator for applying a separating force between the first and second anchor elements. Preferably, the actuator can further include a energy source and a controller for incrementally releasing energy from the source to provide the separating force. The method can be practiced by attaching the first anchor element to a first segment of bone, attaching the second anchor element to a second segment of bone, applying a separating force for a first period of time, measuring a change in distance between the first and second segments of bone, and modifying either the magnitude of the separating force or the period of time to maintain a desired distraction protocol.

In yet another aspect, the invention can use miniature hydraulics to produce a fully buried actuator capable of producing curved distraction trajectories. The methods and devices of the present invention can reduce patient responsibility by automating the motion process, permit clinicians to alter the distraction rate as treatment progresses, and reduce distraction time by making the motion virtually continuous.

Further aspects of the invention can include automation of motion, hydraulic motion power, e.g., driven by a spring-loaded hydraulic pump, the use of micro-dispensing valves to control motion, and constructions that permit full implantation of all components. To eliminate the need for large batteries to store electrical energy, the invention can store hydraulic energy in a spring-loaded cylinder. The bone distraction can be performed by small hydraulic actuators. Miniature valves can control flow of fluid to the actuators. All of the motion can be controlled by a small microcontroller which can be accessed directly or through a radio-frequency (RF) link.

Additional objects, advantages, and novel features of the invention will be set forth in part in the description as follows and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides for methods and devices that can be used to treat skeletal deformities by way of distraction osteogenesis. The devices disclosed herein allow for the controlled distraction between two bone surfaces so that new bone can be formed of generated between the two surfaces. The device can store potential energy, and the stored potential energy can be used to operate the device, thereby separating the two bone surfaces. The amount of distraction can be controlled by the device internally, externally, or by a combination of the two. The bone surfaces can be separated so that the nearest edges remain approximately parallel, or alternatively, the bone surfaces can be separated so that the nearest edges form an angle therebetween. A person having ordinary skill in the art would recognize that although the disclosed methods and devices generally discuss distracting bone surfaces, the devices and methods can also be used to contract bone surfaces, for instance to close a gap between two surfaces.

Figure 1:
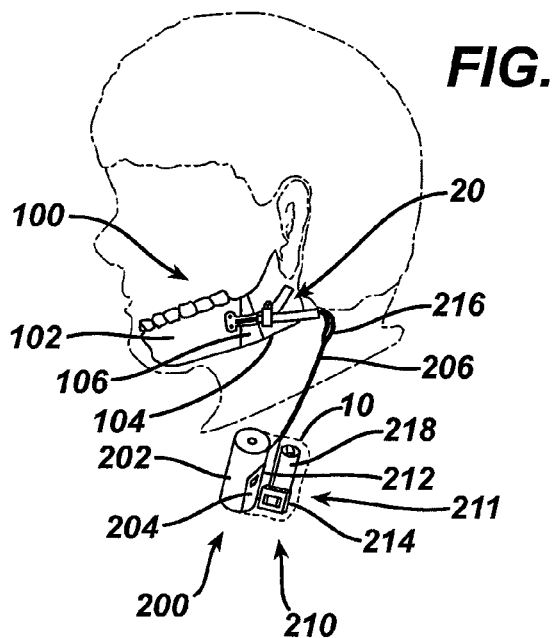
FIG. 1 is a schematic illustration of a mandibular distraction system according to the invention.

While the methods and devices taught can be used in a variety of locations in the body, one place in particular it can be beneficial to use the devices and practice the methods is in the area of the mandible. As illustrated in FIG. 1, a distractor 20 can be anchored to two bone surfaces 102, 104 of a mandible 100 and can be adapted to distract the two surfaces 102, 104 so that new bone 106 can be formed or generated therebetween. In the illustrated embodiment movement of the distractor 20 is caused by an actuation system 200. The actuation system 200 can be disposed in the body and configured to operate based on programmed parameters or operate based on parameters directed to the actuation system 200 from outside of the body. Alternatively, the actuation system 200 can be disposed outside of the body and can be configured to move the distractor 20 remotely. While a number of different components can be used to actuate the distractor 20, the actuation system 200 includes a hydraulic power supply or actuator 202 and a valve 204. The hydraulic power supply 202 can be configured to deliver a fluid to the distractor 20, for example via a tube 206, and the delivery of the fluid can be regulated by the valve 204. The tube 206 can be made of a number of different materials, but in one embodiment it is made of polytetrafluoroethylene. As the amount of fluid delivered to the distractor 20 increases, the distractor 20 moves to further distract the bone surfaces 102, 104.

The amount of fluid that is delivered to the distractor 20 by the actuation system 200 can be controlled in a number of different ways, but in the illustrated embodiment a regulation system 210 is used. As shown, the regulation system 210 and the actuation system 200 are disposed in the same component, control pack 10. Alternatively, the actuation system 200 and the regulation system 210 can be separate components, each being selectively disposed inside or outside of the body. Each of the actuation system 200 and the regulation system 210, or if housed together the control pack 10, can be disposed inside or outside of the body. In one exemplary embodiment, the distractor 20 is disposed inside the body and the control pack 10, including both the actuation system 200 and the regulation system 210 therein, is disposed outside of the body and is configured to communicate signals and/or force to the distractor 20 to distract bone surfaces 102, 104. In the illustrated embodiment, the actuation system includes a controller 211 having a position sensor interface 212, a control circuit 214, a wire 216, and a power supply 218. The position sensor interface 212 can determine the location of at least one of the bone surfaces 102, 104 and a relevant component of the distractor 20, and the control circuit 214 can communicate with the valve 204 of the actuation system 200 to regulate an amount of fluid delivered to the distractor 20. The location of at least one of the bone surfaces 102, 104, and the relevant component of the distractor 20 can be communicated to the position sensor interface 212 in a number of ways, but in the illustrated embodiment wire 216 is connected to a sensor (not illustrated) disposed in the distractor 20 and communicates the location of the distractor 20 to the regulation system 210. The wire 216 can be disposed in the tube 206, separate from the tube 206, or both the tube 206 and the wire 216 can be disposed together in a separate tube. In alternative embodiments, the distractor 20, or one of the bone surfaces 102, 104, can be adapted to communicate a position thereof wirelessly. The power supply 218 can be used to power at least one of the position sensor interface and the control circuit, and can also be used to power components of the actuation system 200 when components of the actuation system 200 may require a power supply.

Figure 2:
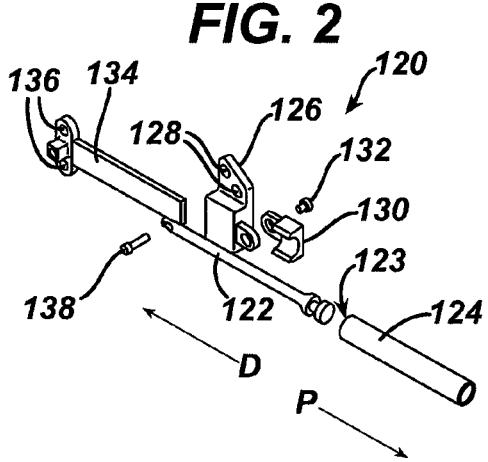
FIG. 2 is an exploded view of one embodiment of a hydraulically-actuated mandibular distractor according to the invention.
Figure 3:
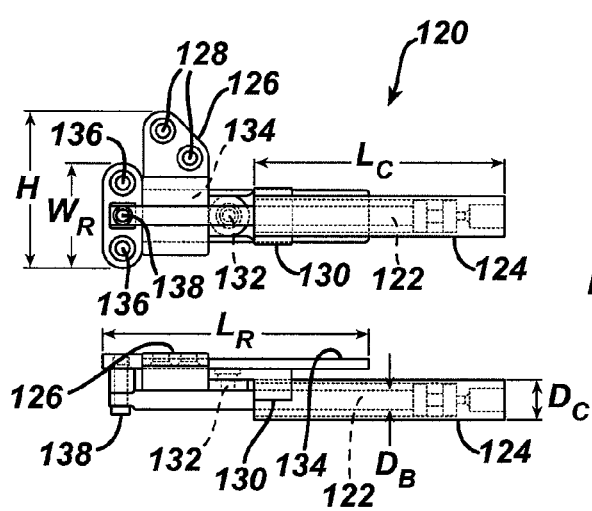
FIG. 3 illustrates side and top views of the distractor of FIG. 2 in a contracted position.

One exemplary embodiment of a distractor 120 is illustrated in FIGS. 2 and 3. The distractor 120 is hydraulically-driven by placing a hydraulic force on a piston 122 disposed in a cylinder 124. An o-ring or other sealing device can be used as a seal between the piston 122 and a bore 123 of the cylinder 124. The cylinder 124 can be configured to receive a fluid such that as fluid enters the cylinder 124, the piston 122 is driven out of the cylinder 124 in a distal direction D. In one embodiment, the cylinder 124 is machined to accept MINSTAC (Miniature Inert System of Tubing and Components) fittings to allow fluid to enter the cylinder 124. MINSTAC fittings are commercially available from the Lee Company in Westbrook, Conn. and are discussed in further detail below with respect to FIGS. 5A and 5B. The cylinder 124 can be coupled to a rail receiving element or slider 126 which is slidably operative to move two bone surfaces with respect to each other that are attached to the distractor 120. The rail receiving element 126 can include features for mating the rail receiving element 126 to a bone surface, such as openings 128. Cortical screws or pins, or other attachment mechanisms, can be disposed through the openings 128 to mate the rail receiving element 126 to a bone surface. In the illustrated embodiment, a saddle 130 is coupled to the cylinder 124 and the saddle 130 is also coupled to the rail receiving element 126, for example by way of a pivot pin 132. The pivot pin 132 can allow some freedom of motion between the cylinder 124 and the rail receiving element 126. The rail receiving element 126 can move two bone surfaces with respect to each other by translating along a rail 134 that is fixed. The rail 134 can be substantially straight and can include features for mating the rail 134 to a bone surface, such as openings 136. Cortical screws or pins, or other attachment mechanisms, can be disposed through the openings 136 to mate the rail 134 to a bone surface. Further, the piston 122 can be coupled to the rail 134 by way of a pivot pin 138. In the illustrated embodiment, as the piston 122 is driven out of the cylinder 124 in the distal direction D, the rail receiving element 126 translates along the rail 134 in the proximal direction P. In an alternative embodiment, the rail receiving element 126 is not operative to slide and instead is configured to be fixed while the rail 134 is not fixed and instead is operative to slide. Accordingly, in such an embodiment, as the piston 122 is driven out of the cylinder 124 in the distal direction D, the rail 134 is also driven in the distal direction D, away from the rail receiving element 126.

While each of the components of the distractor 120 can be made of a variety of materials, and each component can be made of a different material, in one exemplary embodiment each of the piston 122, the cylinder 124, the rail receiving element 126, the saddle 130, the pivot pins 132, 138, and the rail 134 is machined from Titanium 6A1-4V. Further, while the size of the components can vary, based at least in part on the intended use, in one embodiment particularly useful for distracting mandibles the cylinder 124 has a length $L_C$ of approximately 31 mm and a diameter $D_C$ of approximately 5 mm, while a bore 123 for receiving the piston 122 has a diameter $D_B$ of approximately 4 mm. Further, the rail can have a length $L_R$ of approximately 33 mm and can have a width $W_R$ of approximately 6.35 mm, which can allow for a linear displacement of approximately 25 mm. In one embodiment a height H of the distractor 120 is approximately 8 mm.

Figure 4A:
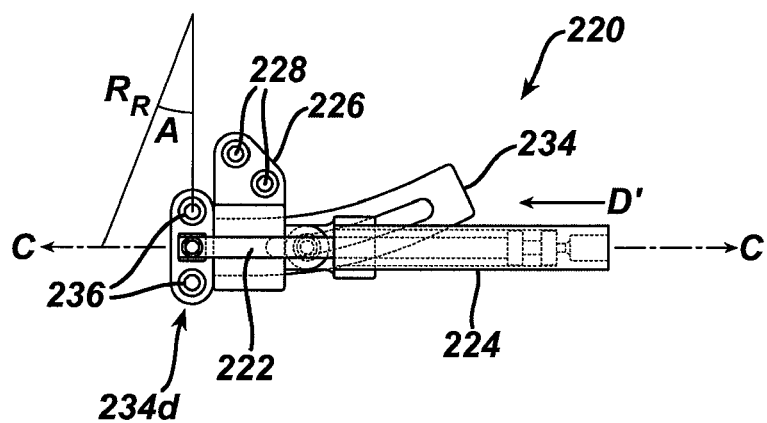
FIG. 4A is a side view of one embodiment of a curved distractor according to the invention in a contracted position.
Figure 4B:
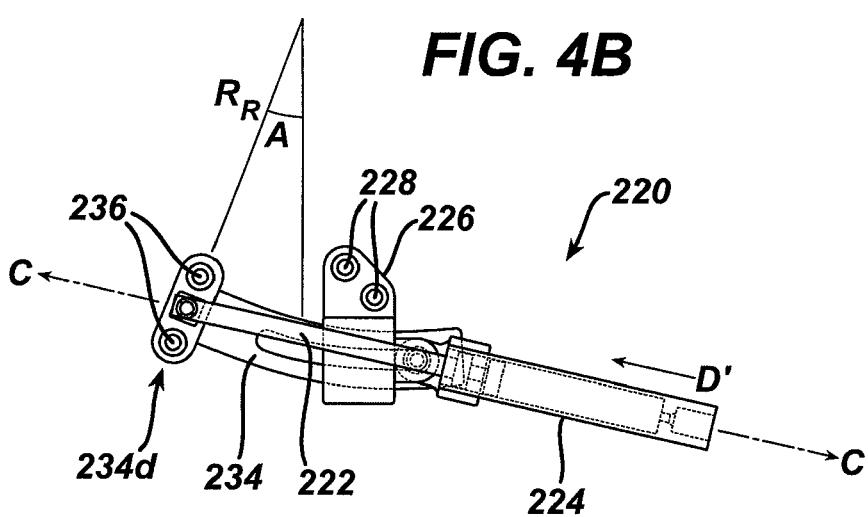
FIG. 4B is a side view of the curved distractor of FIG. 4A in an extended position.

FIGS. 4A and 4B illustrate another embodiment of a distractor 220. The distractor 220 is similar to the distractor 120 in that it includes a piston 222 disposed in a cylinder 224 that is configured to receive a fluid such that as fluid enters the cylinder 224, the piston 222 is driven out of the cylinder in a distal direction D'. Further, the distractor 220 can include a rail receiving element 226 disposed over a rail 234, however rather than the rail receiving element 226 translating over the rail 234, in the illustrated embodiment the rail 234 is coupled to and moves with the piston 222 to move two bone surface with respect to each other while the rail receiving element 226 remains substantially stationary. As illustrated, the rail 234 can pass through rail receiving element 226. The rail 234 can include openings 236 to mate to a bone surface, and the rail receiving element 226 can include openings 228 to mate to another bone surface, for example by inserting cortical screws through the openings 236, 228 and into the respective bone surfaces. While in the distractor 120 the rail 134 is substantially straight, the rail 234 of the distractor 220 is curved, which allows for curvilinear distraction trajectories. FIG. 4A shows the distractor 220 in a contracted position and FIG. 4B shows the distractor 220 in an extended position. As illustrated, the curved rail 234 allows the distractor 220 to displace the nearest edges of bone surfaces at a non-parallel angle, defined herein as an angle of distraction A. More specifically, a distal end 234d of the curved rail 234 can extend outside of an axis C defined by the cylinder when the distractor 220 is moved from the contracted position to the extended position. While the curved rail 234 can have any length and any angle of distraction A, which will depend at least in part on the desired location of the bone surfaces to which the distractor 220 will be mated, in one embodiment the rail 234 has a radius $R_R$ of approximately 50 mm over an angle of distraction A of approximately 32°. Selection of a different angle of distraction A may require a shorter or longer piston 222, cylinder 224, and/or rail 234.

Figure 5:
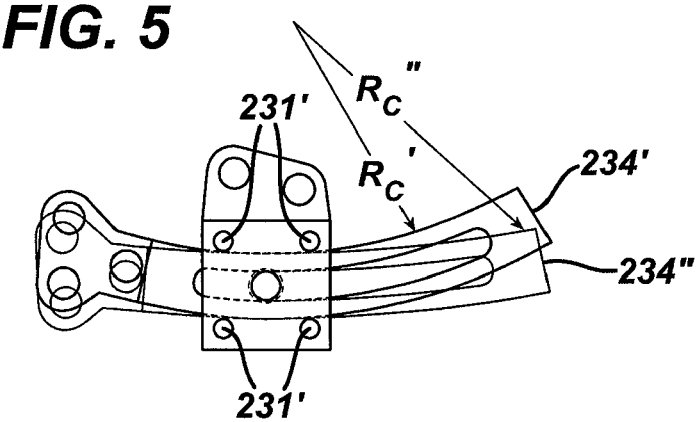
FIG. 5 is a schematic illustration of two curved distractors having different radii of curvature.

As illustrated in FIG. 5, a curved rail 234', 234" of a distractor 220' can be defined by a radius of curvature. Adjusting a radius of curvature of the curved rail 234', 234" can change the angle of distraction A. In the illustrated embodiment, the curved rail 234' has a radius of curvature $R_C'$ of approximately 50 mm, while the curved rail 234" has a radius of curvature $R_C''$ of approximately 75 mm. As shown, the greater the radius of curvature, the less curved the rail 234', 234" is. Each of the curved rails 234', 234" is configured to slide along pivot pins 231', as discussed in further detail with respect to pivot pins 331 in FIGS. 6A and 6B. Selection of a different radius of curvature, like selecting a different angle of distraction, may require a shorter or longer piston, cylinder, and/or rail.

Further, rails of a distractor can be selectively interchangeable such that a kit can be formed that includes a distractor having multiple rails. Each rail can be substituted into the distractor based on the need for a rail having particular dimensions. The rails can be substantially straight and/or curved and can have varying dimensions, for example varying lengths and radii of curvature, to allow for a diverse selection of rails for use with the distractor. The same rail can be used for an entire procedure, or alternatively, rails can be substituted for each other during the course of a procedure, whether the same day or over an extended period of time. Similarly, other components of the distractor can be interchangeable, such as, by way of non-limiting example, the rail receiving element.

Figure 6A:
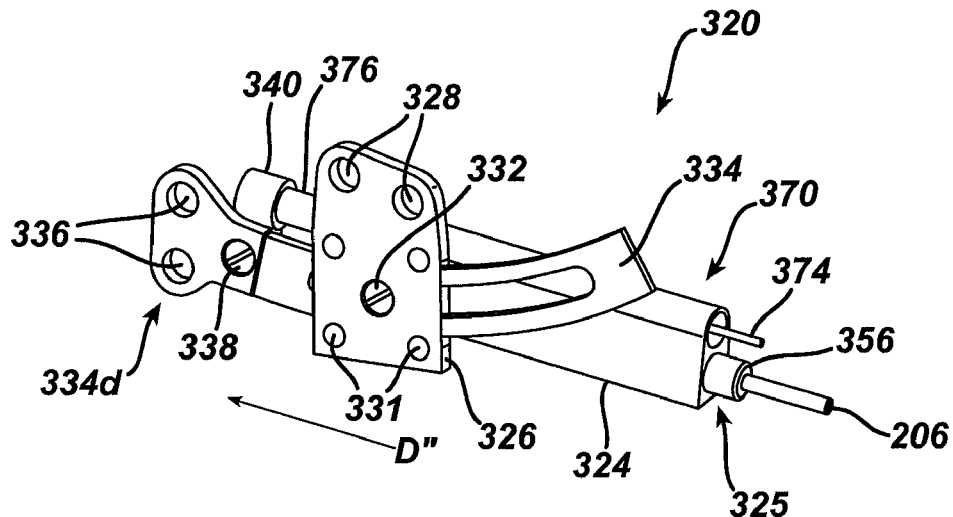
FIG. 6A is a perspective view of another embodiment of a curved distractor according to the invention.
Figure 6B:
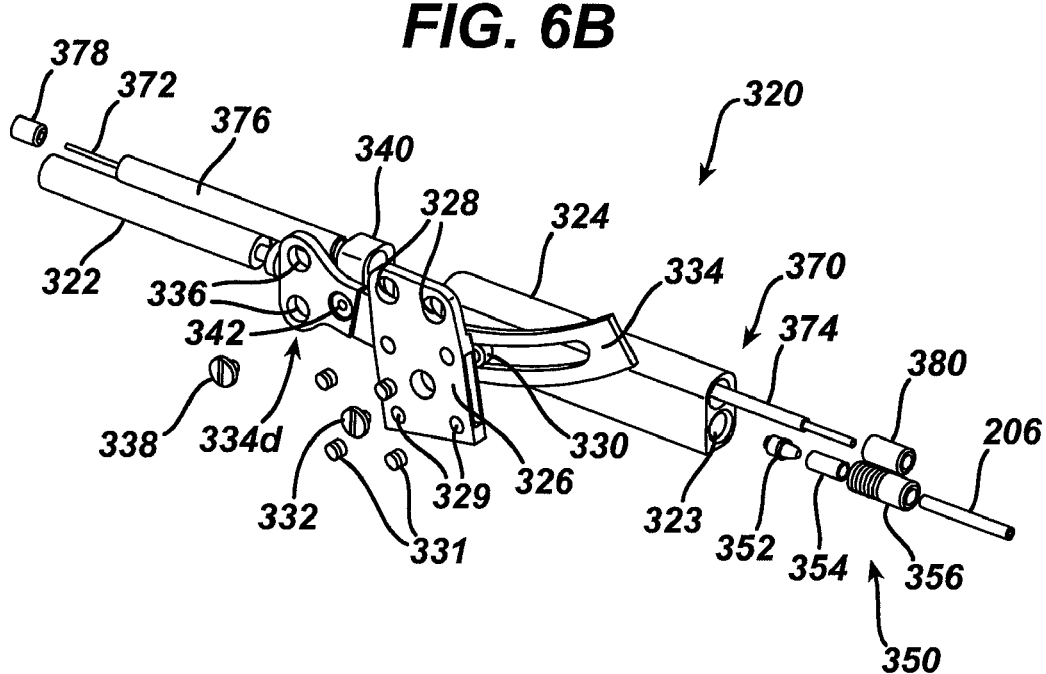
FIG. 6B is an exploded view of the curved distractor of FIG. 6A.
Figure 7:
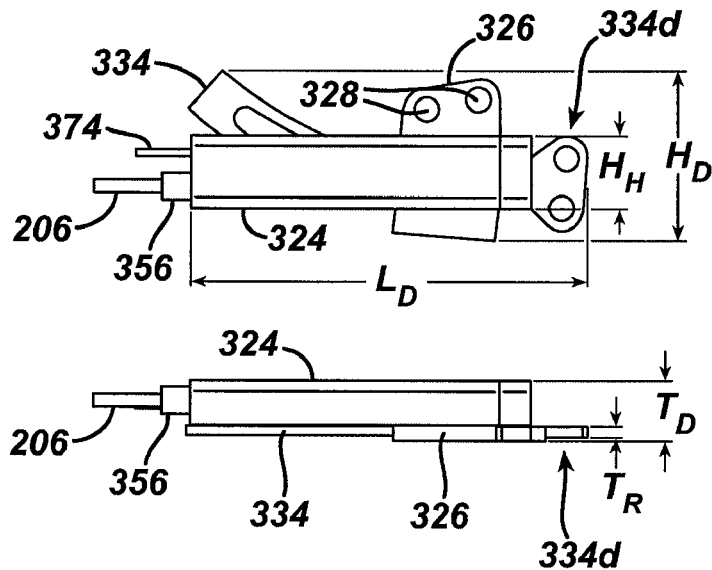
FIG. 7 illustrates side and top views of the curved distractor of FIG. 6A in a contracted position.

Another exemplary embodiment of a distractor 320 is illustrated in FIGS. 6A and 6B. The distractor 320 is hydraulically-driven by placing a hydraulic force on a piston 322 disposed in a housing 324. An o-ring or other sealing device can be used as a seal between the piston 322 and a fluid chamber 323 of the housing 324. The fluid chamber 323 can be configured to receive a fluid such that as fluid enters the chamber 323, the piston 322 is driven out of the chamber 323 in a distal direction D". In the illustrated embodiment, the chamber 323 is also adapted to accept MINSTAC fittings 350. The MINSTAC fittings can include a ferrule 352, a collet 354, and a coupling 356, which together allow the tube 206 of the actuation system 200 (not pictured) to be in fluid communication with the fluid chamber 323 of the housing 324. The housing 324 can be configured to mate to a bone surface. In the illustrated embodiment the housing is coupled to a rail receiving element 326 that includes features for mating the rail receiving element 326, and thereby the housing 324, to a bone surface. In the illustrated embodiment the features for mating the rail receiving element 326 to a bone surface are openings 328. The openings 328 can be offset from each other. Cortical screw or pins, or other attachment mechanisms, can be disposed through the openings 328 to mate the rail receiving element 326 to a bone surface.

The housing 324 can include a pivot 330 such that a pivot pin 332 can mate the rail receiving element 326 to the housing 324 by way of the pivot 330. The pivot pin 332 can allow some freedom of motion between the housing 324 and the rail receiving element 326. A rail 334 can be coupled to each of the piston 322 and the housing 324 such that as the piston 322 moves in the distal direction D", the rail 334 also moves away from the housing 324 to increase a gap between a distal end 334d of the rail 334 and the housing 324. The rail receiving element 326 can further include one or more pin-receiving apertures 329. As illustrated, the rail 334 can pass through rail receiving element 326 and can pivot along one or more pivot pins 331 disposed in the one or more pin-receiving apertures 329. In embodiments that utilize more than one rail, the rails can each be configured to slide on the same pivot pins 331 without requiring movement of the pivot pins 331, as shown in FIG. 5 with respect to rails 234', 234". The distal end 334d of the rail 334 can include features for mating the rail 334 to a bone surface, such as openings 336. The openings 336 can be offset from each other. Cortical screw or pins, or other attachment mechanisms, can be disposed through the openings 336 to mate the rail 334 to a bone surface. Further, a piston anchor 340 having a pivot 342 can couple the piston 322 to the rail 334 by way of a pivot pin 338. The pivot pin 338 can allow some freedom of motion between the piston 322 and the rail 334. In the illustrated embodiment, as the piston 322 is driven out of the cylinder 324 in the distal direction D", the rail 334 travels along the pivot 330 of the housing 324 such that the distal end 334d of the rail 334 moves away from the housing 324 at an angle because the rail 334 is curved. In an alternative embodiment, the rail 334 is fixed and instead the rail receiving element 326 is configured to translate along a length of the rail 334. In such an embodiment, the rail 334 can be substantially straight or curved and the rail receiving element 326 can be specifically designed to slide across the shape of the rail 334. Accordingly, as the piston 322 is driven out of the cylinder 324 in the distal direction D", the rail receiving element 326 translates along the fixed rail 334 away from the distal end 334d of the rail 334.

The illustrated embodiment also includes a sensing mechanism 370 configured to determine a location of a relevant component of the distractor 320. While in the illustrated embodiment the relevant components include the piston 322 and the rail 334, in other embodiments, such as an embodiment in which the rail receiving element 326 translates across the rail 334, the rail receiving element 326 can be a relevant component for determining a location. As shown, the sensing mechanism 370 includes a transducer core 372 coupled to a transducer coil 374. The transducer core 372 is coupled to both the piston 322 and the rail 334 such that movement of the piston 322, and thereby the rail 334, causes movement of the transducer core 372. As the core 372 moves in the distal direction D", the core 372 moves away from the coil 374, thereby reducing the inductance of the coil 374. In the illustrated embodiment, the transducer core 372 and the transducer coil 374 are at least partially disposed in a sensing chamber 325 of the housing 324. Further, as shown, a shield 376 is coupled to the transducer core 372 and the combination of the shield 376 and the transducer core 372 is coupled to both the piston 322 and the rail 334 by the piston anchor 340. A distal core anchor 378 can be used to maintain the shield 376 and the transducer core 374 in the sensing mechanism attachment anchor 340, while a proximal core anchor 380 can be used to maintain the transducer coil 374 in a desired location of the sensing chamber 325. The transducer coil 374 can be configured to communicate the location of the transducer core 372 to a location remote from the distractor 320. For example, as the inductance of the transducer coil 374 changes, the coil 374 can be wired to a position sensor interface of a regulation system, such as the position sensor interface 212 of the regulation system 210 (not pictured), which can in turn regulate an actuation system, such as actuation system 200 (not pictured), to allow for further distraction as desired. Alternatively, the transducer coil 374 can be configured to communicate wirelessly with a regulation system and/or an actuation system like the regulation system 210 and the actuation system 200.

Similar to the distractor 120, the distractor 320 can be made of a variety of different materials, including Titanium 6A1-4V, and each component of the distractor 320 can be made of a different material. In one exemplary embodiment, each of the piston 322, the cylinder 324, the rail receiving element 326, the pivot pins 331, 332, and 338, the rail 334, the piston anchor 340, the collet 354, the coupling 356, and the shield 376 is machined from 316L stainless steel, the ferrule 352 is machined from polytetrafluoroethylene, and each of the core anchors 378, 380 is machined from ultra high molecular weight polyethylene. Further, while the size of the components can vary, based at least in part on the intended use, in one embodiment particularly useful for distracting mandibles a length $L_D$ from a proximal end of the housing 324 to a distal end 334d of the rail 334 in the contracted position is approximately 46.5 mm, a height $H_D$ from a tip of the rail 334 to a bottom of the rail receiving element 326 is approximately 20 mm, a height $H_H$ of the housing 324 is approximately 8.75 mm, a thickness $T_D$ of the distractor 320 is approximately 7.25 mm, and a thickness $T_R$ of the rail 334 is approximately 1.5 mm.

Figure 8:
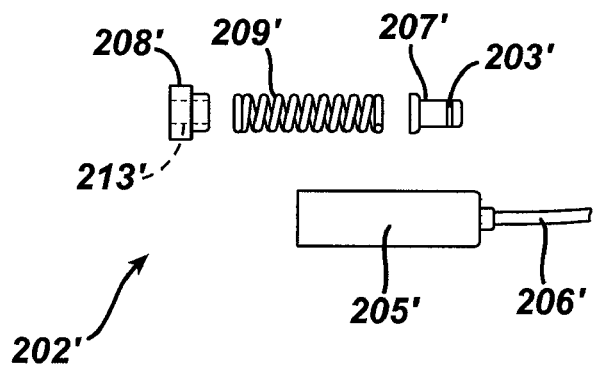
FIG. 8 is an exploded view of one embodiment of a hydraulic power supply with a spring-loaded reservoir.
Figure 9:
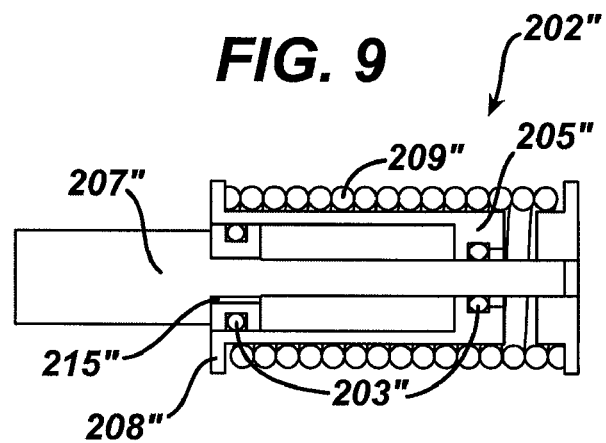
FIG. 9 is a cross-sectional view of another embodiment of a hydraulic power supply with a spring-loaded reservoir.

FIGS. 8 and 9 illustrate exemplary embodiments of a hydraulic power supply or actuator 202', 202" having a spring-loaded reservoir for use in an actuation mechanism, like the actuation mechanism 200, with a distractor, such as the distractors 20, 120, 220, and 320. In particular, the hydraulic power supplies 202', 202" are configured to be driven by pressurized fluid, such as water, provided from the spring-loaded reservoir. In the illustrated embodiments, the hydraulic power supplies 202', 202" include a housing 205', 205" a piston 207', 207" at least partially disposed in the housing 205', 205", a spring 209', 209" disposed in the housing 205', 205" and configured to apply a force to the piston 207', 207", and a cap 208', 208" configured to keep the spring 209', 209" disposed in the housing 205', 205" and further configured to allow a force being supplied to the spring 209', 209" to be adjusted, either by the cap 208', 208" itself or by an outside agent. As shown in FIG. 9, the cap 208" is integrally formed with the housing 205". Optionally, the piston 207', 207" can be sealed with one or more seals 203', 203", such as an o-ring made of silicone or a Viton o-ring. The piston 207', 207" can also optionally be lubricated with a surgical lubricant. With respect to the hydraulic power supply or actuator 202' of FIG. 8, an adjustment mechanism, such as a threaded rod, can be introduced into the housing 205' through an opening 213' of the housing 205' to charge the supply, i.e. to pull the piston 207' toward the cap 208', thereby drawing in a fluid and compressing the spring 209'. As shown, a force being applied to the spring 209' can be adjusted by turning the cap 208'. As the force on the spring 209' increases, a force being applied to the piston 207' by way of the spring 209' also increases, which in turn can cause fluid to be displaced out of the housing 205'. A tube 206' can be coupled to the housing 205' to receive the displaced fluid and direct it to the distractor. As illustrated in particular by FIG. 9, the piston 207" can extend out of the housing 205" such that an adjustment mechanism does not have to be introduced into the housing 205". As shown by FIG. 9, the location of the piston 207" can be adjusted directly from outside of the housing 205". The piston 207" can also be generally configured to stay in place. Further, the piston 207" can include a fluid passage 215", which can be configured to add or remove fluid from the housing 205" as desired.

As discussed generally with respect to the actuation system 200, a hydraulic power supply or actuator 202 can be regulated by a valve 204. Likewise, the hydraulic power supply 202', 202" can also be regulated by one or more valves. More than one valve can be used in instances where it may be desirable to either add or remove fluid from a distractor. The one or more valves can be coupled to the hydraulic power supply 202', 202" to control the flow of fluid therefrom. Various valves can be employed. For example, a micro-dispensing valve configured to operate with the MINSTAC fittings discussed above, such as model INKX0520950AA from the Lee Company, can be used. In one embodiment, the valve can be coupled to the hydraulic power supply 202', 202" with a tube, such as 1/16 inch polytetrafluoroethylene tubing. Further, any sort of circuit can be used to operate the valve. For example, a simple single-transistor switch circuit can be used to control current to the valve from a TTL-level input.

Figure 10:
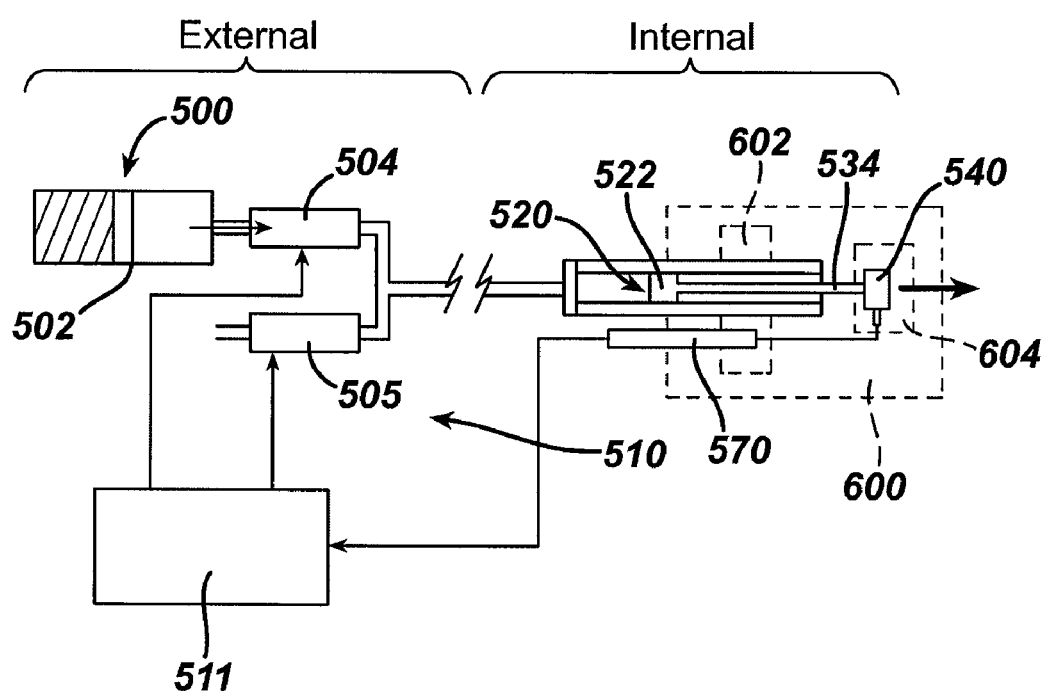
FIG. 10 is a schematic illustration of one embodiment of a system for distracting bones.

FIG. 10 illustrates a schematic view of a distractor 520 coupled to an actuation system 500 and a regulation system 510. The actuation system 500 and the regulation system 510 can be disposed within a control pack, like the control pack 10. Each of the distractor 520, the actuation system 500, and the regulation system 510 can include components similar to the components discussed herein. By way of non-limiting example, the distractor 520 can be similar to the distractors 20, 120, 220, and 320. As shown, the distractor 520, which includes a piston 522, a rail 534, a piston anchor 540, and a sensing mechanism 570, is disposed between two bone surfaces 602, 604 of a mandible 600. The distractor 520 is in fluid communication with the actuation system 500, and in particular a hydraulic power supply 502, by way of a tube 506. Disposed therebetween can be one or more valves 504, 505 of the regulation system 510, which are configured to regulate a flow of fluid from the hydraulic power supply 502 to the distractor 520. In the illustrated embodiment, the valve 504 is configured to allow fluid to flow toward the distractor 520 while the valve 505 is a reverse valve which allows fluid to be evacuated from the distractor 520. While the reverse valve 505 can be configured to allow fluid removed from the distractor 520 to go back to the hydraulic power supply 502, in the illustrated embodiment fluid received from the distractor 520 is removed from the system. The valves 504, 505 can be controlled based on feedback received from the sensing mechanism 570. More particularly, the sensing mechanism 570 can be wired to communicate with a controller 511, for example a DSPIC30F6012A microcontroller from the Lee Company, to analyze a location of the rail 534. Although not illustrated, similar to the controller 211, the controller 511 can include components such as a position sensor interface, a control circuit, a wire, and a power supply. Based on the feedback received from the sensing mechanism 570 and analyzed by the controller the valves 504, 505 can be operated to control fluid flow between the actuation system 500 and the distractor 520. Such control can be programmed to occur automatically, or alternatively, can be performed manually.

A person having ordinary skill in the art would recognize that the system discussed with respect to FIG. 10 is merely one of many systems that can be designed based on the teachings herein. By way of non-limiting example, although the controller 511 is configured to control the valves 504, 505, in an alternative embodiment the controller 511 can be configured to control a force being applied to a spring of the hydraulic power supply 502. By further way of non-limiting example, although the system as illustrated shows only the distractor 520 being an internal device, in alternative embodiments the components of the actuation system 500 and the regulation system 510 can be configured to be disposed internally.

A system similar to the one described with respect to FIG. 10 was used in tests of the distractor 320 and the hydraulic power supply 202'. In particular, the controller 511 measured the inductance of the coil 374 at fifteen minute intervals and opened a valve 504, which happened to be a solenoid valve, for a time interval proportional to the error between the desired and measured position.

At full compression of the spring 209' the fluid pressure was approximately 3.5 MPa, producing a force of the piston 322 of approximately 40 N. At full extension of the spring 209' the fluid pressure was approximately 2.0 MPa, producing a force of the piston 322 of approximately 25 N. These tests demonstrated that the hydraulic power supply 202', the MINSTAC fittings, valves 504, 505, tubes 206', and distractor 320 can survive the required pressures.

The system described with respect to FIG. 10 was further used to test the distractor 320 in pig cadavers and live animals to evaluate surgical installation and operation. During the course of the testing, the system functioned for several days in live animals and was able to produce forces necessary to complete a distraction to approximately 11 mm.

In an 11 day-1 millimeter per day distraction performed on one pig cadaver using the system described with respect to FIG. 10 with the distractor 320, the controller 511 was able to follow a programmed motion with a root-mean-squared error of approximately 0.086 mm. Further, in a live animal, surrounding tissue grows and stretches to accommodate new bone.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A device for distraction osteogenesis comprising;
 a first anchor element adapted to be attached to a first segment of bone,
 a second anchor element adapted to be attached to a second segment of bone, and an actuator for applying a separating force between the first and second anchor elements, the actuator further comprising
 a reservoir of pre-charged, pressurized fluid, wherein the reservoir is configured such that the fluid therein can be pressurized prior to the reservoir being implanted at an implantation site; and
 a controller that opens a valve for periods of time to regulate flow of the fluid to provide the separating force, wherein the separating force is effective to increase the distance between the first and second segments of bone to an extent effective to induce osteogenesis between the first and second segments of bone.

2. The device of claim 1 wherein the first anchor element further comprises a rail and the second anchor element is mechanically linked to the rail of the first anchor element.

3. The device of claim 2 wherein the second anchor element is slidably coupled to the rail of the first anchor element.

4. The device of claim 2 wherein the rail is a straight rail.

5. The device of claim 2 wherein the rail is a curved rail.

6. The device of claim 2 wherein the rail is slidably coupled to the second anchor element.

7. The device of claim 6 wherein the rail is a straight rail.

8. The device of claim 6 wherein the rail is a curved rail.

9. The device of claim 1 wherein the actuator further comprises a chamber coupled to one of the anchor elements and a piston disposed within the chamber and mechanically linked to the other anchor element, the chamber being in fluid communication with the reservoir such that fluid flows between the reservoir and the chamber to provide the separating force.

10. The device of claim 1 wherein the reservoir comprises a spring that applies pressure to the fluid disposed therein.

11. The device of claim 1 wherein the actuator further comprises a valve for regulating fluid transfer from the reservoir to a chamber.

12. The device of claim 1 further comprising a sensor for measuring separation of the first and second anchor elements.

13. The device of claim 1 wherein the controller further comprises a microprocessor.

14. A kit for distraction osteogenesis comprising:
 a plurality of base elements adapted to be attached to a first segment of bone, each of said base elements having a rail of a different shape,
 at least one rail receiving element adapted to be attached to a second segment of bone and further adapted to have at least one of the rails of the base elements slidably coupled thereto, wherein at least one of the rails is configured to move one of one of the plurality of base elements and the at least one rail receiving element along a curvilinear trajectory with respect to the other of one of the plurality of base elements and the at least one rail receiving element,
 an actuator for applying a separating force between one of the plurality of base elements and the at least one rail receiving element, the actuator further comprising a potential energy storage device and a controller for incrementally releasing energy from the energy storage device to provide the separating force, and a controller that opens a valve for periods of time to regulate flow of fluid to provide the separating force, wherein the separating force is effective to increase the distance between the first and second segments of bone to an extent effective to induce osteogenesis between the first and second segments of bone.

15. A device for distraction osteogenesis comprising:
 a first anchor element adapted to be attached to a first segment of bone,
 a second anchor element adapted to be attached to a second segment of bone,
 an actuator for applying a separating force between the first and second anchor elements such that the one of the first and second anchor elements moves along a curvilinear trajectory with respect to the other of the first and second anchor elements, the actuator further comprising a potential energy storage device and a controller that opens a valve for periods of time to regulate flow of fluid to provide the separating force, wherein the separating force is effective to increase the distance between the first and second segments of bone to an extent effective to induce osteogenesis between the first and second segments of bone.

16. The device of claim 15, wherein the first anchor element further comprises a curved rail mechanically linked to the second anchor element.

17. A device for distraction osteogenesis comprising:
 a first anchor element adapted to be attached to a first segment of bone,
 a second anchor element adapted to be attached to a second segment of bone, and
 an actuator for applying a separating force between the first and second anchor elements, the actuator further comprising:
  a chamber coupled to one of the first anchor element and the second anchor element;
  a piston disposed within the chamber and mechanically linked to the other of the first anchor element and the second anchor element;
  a reservoir of fluid in fluid communication with the chamber;
  a valve for regulating fluid flow between the reservoir and the chamber;
  a sensor for measuring separation of the first and second anchor elements;
  a controller that opens the valve for periods of time based on a measurement by the sensor to regulate the fluid flow between the chamber and the reservoir to provide the separating force, wherein the separating force is effective to increase the distance between the first and second segments of bone to an extent effective to induce osteogenesis between the first and second segments of bone.

18. The device of claim 17, wherein one of the first and second anchor elements is configured to move along a curvilinear trajectory with respect to the other of the first and second anchor elements.

19. The device of claim 17, wherein the fluid disposed in the reservoir is a pre-charged, pressurized fluid.

20. The device of claim 1, wherein a pressure of the fluid in the reservoir is at least about 2.0 MPa.

* * * * *